United States Patent [19]

Barabas

[11] Patent Number: 4,684,519
[45] Date of Patent: Aug. 4, 1987

[54] METHOD OF PREPARING A POLYVINYLPYRROLIDONE-HALOGEN COMPLEX OF IMPROVED STABILITY

[75] Inventor: Eugene S. Barabas, Watchung, N.J.

[73] Assignee: GAF Corporation, Wayne, N.J.

[21] Appl. No.: 849,918

[22] Filed: Apr. 9, 1986

[51] Int. Cl.$^4$ .............................................. A61K 31/79
[52] U.S. Cl. ...................................... 424/80; 424/150
[58] Field of Search ................................... 424/80, 150

[56] References Cited

U.S. PATENT DOCUMENTS

| | | | |
|---|---|---|---|
| 4,125,602 | 11/1978 | Atasoy et al. | 424/80 |
| 4,235,884 | 11/1980 | Salkin | 424/150 |
| 4,320,114 | 3/1982 | Denzinger et al. | 424/80 |

Primary Examiner—Leonard Schenkman
Attorney, Agent, or Firm—Marilyn J. Maue; Joshua J. Ward

[57] ABSTRACT

The invention relates to the process for making a highly stable polyvinylpyrrolidone-halogen complex by forming a reaction solution in a diffusion zone containing a 3 to 9 percent aqueous solution of polyvinylpyrrolidone and halogen dissolved in an alcohol solution wherein the concentration of alcohol is not less than 40% of the total solutions and wherein a portion of the halogen requirement, up to 35%, may be in the form of hydrogen halide or a salt thereof; reacting the polypyrrolidone and halogen components and forming a water/alcohol azeotrope simultaneously with the corresponding polyvinylpyrrolidone-halogen complex; subjecting the reacted mixture to azeotropic distillation to remove an aqueous alcohol distillate; recycling the distillate to the halogen solubilizing or diffusion zone and subjecting the remaining liquid product solution, containing not more than about 35% solids, to spray drying to recover the polyvinylpyrrolidone/halogen product in the form of a particulate solid wherein each particle is of a uniform brownish yellow color throughout.

7 Claims, No Drawings

METHOD OF PREPARING A POLYVINYLPYRROLIDONE-HALOGEN COMPLEX OF IMPROVED STABILITY

The present invention relates to a method for the preparation of complexes of polyvinylpyrrolidone and halogens having improved stability, and a process providing more efficient use of halogen in the preparation of said complex. In a more particular aspect, the invention relates to the preparation of a polyvinylpyrrolidone-iodine complex of greatly improved stability.

BACKGROUND OF THE INVENTION

The complex of polyvinylpyrrolidone-iodine (PVP-I) is well known for its antiseptic properties resulting from the slow release of active iodine. This complex is particularly valuable since it is non-toxic and non-irritating to the skin. However, improvement in the stability of the complex for up to about one month storage with less than 6% loss of iodine is highly desirable.

The PVP-bromine-I and PVP-chlorine-I complexes are also useful as bleaching agents, bactericides, germicides and antiseptics and are also included within the scope of this application.

Various techniques have been proposed for the preparation of these complexed compounds such as the solution reaction of PVP and halogen in toxic or malodorous liquid solvents, such as methylene chloride. To improve stability and product purity, U.S. Pat. No. 4,125,602 proposes a multiphase reaction wherein a colloidal suspension of PVP in one solvent is reacted with iodine dissolved in another solvent. While improved stability is achieved, this process is not commercially attractive since the reaction, which takes place only on the interface of the multiple phases, is extremely slow and efficient use of the reactive species in the overall reaction mixture beyond the interfacial zone, is not realized. The process of U.S. Pat. No. 4,235,884 proposes the use of expensive, water insoluble solvents such as ethyl chloride, chloroform, acetone or methylene chloride alone or in admixture. While both of the latter processes improve product stability, they generally do not satisfy the desired standard of not more than 6% loss of iodine over a period of several days.

Accordingly, it is an object of this invention to overcome all of the above disadvantages in a process for the preparation of the PVP-halogen compexes.

Another object of this invention is to produce a polyvinylpyrrolidone/halogen complex compound in particulate form which particles have a uniform complexed composition throughout.

Another object of this invention is to greatly improve the efficient use of the process reactants to provide the highest conversion based on reactants fed to the system.

Still another object of the invention is to provide an economical and commercially feasible process culminating in the preparation of PVP-I product having significantly improved stability.

These and other objects of the invention will become apparent from the following description and disclosure.

According to this invention there is provided a homogeneous liquid phase process for preparing PVP-halogen complexes which comprises the steps of dissolving aqueous PVP and halogen containing 0 to 40% halide in a preformed $C_{1-4}$ alcohol solution wherein the concentration of alcohol in the resulting mixture is at least 40%, preferably between about 50 and 95% ethanol or methanol/ethanol mixture. Dissolving the halogen to provide the preformed solution is effected by dissolving halogen inthe alcohol at a temperature of from about 50° to about 75° C. and mixing for a period of from about 1 to 5 hours.

The resulting PVP and iodine or halogen solution is then reacted at a temperature between 50° C. and about 95° C. under atmospheric pressure for a period of from about 1 to about 10 hours, preferably between about 80° C. and about 90° C. for a period of from about 1.5 to about 6 hours, under conditions such that a water/alcohol azeotrope is formed simultaneously with the PVP-halogen complexed product. The azeotrope is stripped from the liquid product mixture at a stripping temperature of between about 85 and about 98° C. for a period of from about 1 to about 3 hours, under atmospheric pressure or lower temperatures under more elevated pressures, e.g. up to about 50 mm Hg. The stripping zone may be a packed or unpacked column; the former providing additional reflux in the distillation zone. Stripping may be continued until the solids content in the remaining distilland reaches a critical limit, usually not more than 35% solids. However, to maintain a lowered solids content in the distilland, preferably between about 15 and about 30%, deionized water can be added to the liquid product mixture either during or after stripping. Because of the efficient use of reactants in the present process, the liquid product mixture from the reactor usually contains a considerable amount of solids. In any case, the solids content in the distilland should not be permitted to exceed 40% before spray drying.

The distillate from the stripping zone is then recovered and employed to dissolve additional halogen before entry into the reaction zone. If desired, the distillate may be subjected to drying to remove substantially all or a portion of water before recycle to the halogen dissolving zone. The remaining liquid product mixture is then spray dried to produce a substantially pure product as a particulate solid whose particles have a uniform brownish color, indicating iodination of the PVP throughout the particle. The resulting products of this invention exhibit less than 3% halogen, e.g. iodine, loss after 20 days standing and less than 5% halogen, e.g. iodine, loss after one month.

While other methods of drying the liquid product mixture such as evaporation, freeze drying etc., may be employed, spray drying is preferred. Generally, spray drying is accomplished at an air inlet temperature of from about 250° C. to about 400° C. under an air pressure of from about 4 Kg/cm² to about 7 Kg/cm² and an outlet air temperature of from about 98° C. to about 175° C. The dryer is equipped with an atomizing wheel or other device adapted to spray liquid product.

In the above process, up to 35% of the halogen requirement in the form of hydrogen halide, e.g. hydrogen iodide or an inorganic halide salt, thereof such as a sodium or potassium salt (e.g. NaI and KI) can be employed; however, 40% halide leads to product defficient in available halogen and is to be avoided.

Because of the infinite solubility of halogen, particularly iodine in alcohol, and the critical alcohol concentration in the reaction zone of not less than 40%, the iodine vapor pressure is maintained at substantially zero and the need for iodide supplement to the system is obviated. Accordingly, the reaction can be run in the total absence of iodide; although a small amount of hydrogen halide, e.g. HI or salt thereof is desirable to eliminate halogen loss at later stages of product purification. Also, corrosion problems are overcome due to the rapidity of the homogeneous liquid phase reaction, usually about 1.5 hours, so that simple glass lined or stainless steel equipment can be used.

Contrary to prior teaching, the formation of the alcohol/water azeotrope is a benefit in the present process and is used to provide an inexpensive and efficient means of reducing the liquid product volume and to provide recycle having the essential alcohol/water proportions suitable for solubilizing additional halogen, e.g. iodine or iodine and iodide mixtures prior to reaction with aqueous PVP. The removal of the aqueous alcohol azeotrope also eliminates the presence of highly flammable or toxic vapors and other hazards which may be encountered during subsequent air or spray drying of the product solution.

The polyvinylpyrrolidone feed employed in this process is a relatively pure polymer having a number average molecular weight between about 15,000 and about 500,000 and a K value of from about 12 to about 100, preferably from about 20 to about 60. The polyvinylpyrrolidone is prepared from vinylpyrrolidone monomer in an aqueous solution of isopropyl alcohol and in the presence of an organic peroxide catalyst, such as ditertiary butyl peroxide catalyst. The PVP product most preferably has a K value between about 26 and 35 and a pH in 5% aqueous solution of from 3 to 7. Also, it is desirable that the PVP feed have an APHA color rating in 5% aqueous solution not in excess of 40 and metal impurities less than 30 ppm.

The alcohol most suitably employed in the present process is standard grade ethanol, which dissolves not only PVP, iodine, and iodides but also the $I_3$ complex which is temporarily formed in the reaction mixture and which is kept solution and in equilibrium with iodine and iodide ion throughout the reaction.

The remaining reaction conditions are conventional and include a ratio of iodine+iodide to PVP within the range of from about 1:3.5 to about 1:5, preferably between about 1:3.8 and about 1:4.8 and a halogen concentration of from 65 to 100% with respect to halide. These conditions are also observed in carrying out the present process.

Having thus described the invention, reference is now had to the following Examples which set forth particular and preferred embodiments of the invention but which are not to be construed as limiting to its scope which is more broadly defined above and in the appended claims.

EXAMPLE 1

A solution of 789.4 g. of iodine in 644 g. of ethanol was prepared by heating to 70±5° C. for 2 hours in a glass lined kettle equipped with a dropping funnel. An aqueous 57% solution of 68.6 g. of HI was then added to the solution through the dropping funnel. The resulting solution was then charged in a period of 2 minutes to a glass reactor maintained at about 85° C. The glass reactor which was equipped with an agitator and a reflux condenser, contained an aqueous 35% solution of 2214 g. of polyvinylpyrrolidone (PVP), K30*. The solutions introduced into the reactor provided a PVP:$I_2$+HI mole ratio of 4.5:1 and the HI represented 25-30% of the total iodine requirement.

| *Analysis of PVP feed: | |
|---|---|
| Molecular Weight | 15,000–30,000 |
| pH | 3–7 |
| Ash | 0.02% USP |
| Aldehydes | 0.2% |
| Vinylpyrrolidone | 0.2% |
| Moisture | 5% |
| Nitrogen | 11–13% |
| APHA color | 30 maximum |
| Arsenic | 10 ppm maximum |
| Lead | 10 ppm maximum |

The resulting solution was then refluxed at the azeotrope temperature 85°–86° C. for 1.25 hours to completion of the complexing.

Following the 90 minute reaction step, the ethanol/water azeotrope was stripped off while continuously replacing the removed portion with deionized water. Solvent stripping was continued until the bath temperature reached 98° C., at which time the system was returned to reflux conditions and held at reflux until a total of 90 minutes of combined distillation and reflux had been completed. At this point, approximately 90% of the solvent had been removed, and the total distillate was 1.6–1.8 times the initial ethanol/methanol charge. Cool, deionized $H_2O$ was immediately added to the stripping zone to bring the final solids concentration down to 24% in preparation for spray drying.

The azeotrope was recycled to the $I_2$ solution kettle for continued dissolution of iodine feed before reaction with additional PVP in the reactor. Make-up ethanol was also added to the kettle along the required amount of iodine. The alcohol to iodine ratio was maintained at 4:1 regardless of the water content.

After stripping, the liquid product mixture had approximately the following composition:

| PVP-I | 24% |
|---|---|
| Water | 74.1% |
| Ethanol | 1.9% |

This product mixture was spray dried (atomizing wheel or 2-fluid nozzle) at an inlet air temperature of 285° C. and an outlet air temperature of 120° C. The feed rate to the spray dryer was 15 ml/min and the final product contained approximately 96% solids, <200 ppm ethanol and 50 ppm methanol.

EXAMPLES 2–7

The above process was repeated except for variations in the PVP:$I_2$+HI ratios and % HI, noted in following Table I. The stability of the final products of each example were determined by % $I_2$ loss and retention of % available $I_2$ in the product. All of the products of Examples 1–7 were uniformly brownish yellow colored particles (not more than 5% on 40 mesh screen) and contained less than 200 ppm eethanol.

The following determinations were made after 6 hours standing.

TABLE I

| | PVP:I | | Dried Product | | | |
|---|---|---|---|---|---|---|
| | | | % $I_2$ Loss | | % Available $I_2$ | |
| Example | Ratio | % HI | Range | Mean | Range | Mean |
| 2 | 4:1 | 20 | 1.5–2.3 | 1.8 | 11.7–13.2 | 12.5 |
| 3 | 4:1 | 0 | — | 1.4 | — | 11.2 |
| 4 | 4:1 | 10 | — | 1.6 | — | 11.8 |

TABLE I-continued

| | PVP:I | | Dried Product | | | |
|---|---|---|---|---|---|---|
| | | | % I₂ Loss | | % Available I₂ | |
| Example | Ratio | % HI | Range | Mean | Range | Mean |
| 5 | 4.1:1 | 35 | 1.7-2.5 | 2.2 | 12.2-13.6 | 12.9 |
| 6 | 4.5:1 | 30 | 1.7-3.2 | 2.2 | 9.2-12.0 | 10.4 |
| 7 | 4.5:1 | 25 | 1.9-2.7 | 2.1 | 9.9-10.7 | 10.4 |

The data indicate that PVP-I produced by the solution iodination process had consistently excellent stability (2±0.5% vs <3.0 spec.), as measured by the 6 hour % I₂ loss method.

Twenty day stability tests were preformed on the samples of Examples 6 and 7. The results were 3% and 2.7% I₂ loss respectively.

What is claimed is:

1. A homogeneous liquid phase process for preparing polyvinylpyrrolidonehalogen complexes of improved stability which comprises the steps:
   (a) dissolving a vinylpyrrolidone polymer having a K value between about 12 and about 100 in about 3 to about 9 percent by weight water;
   (b) dissolving halogen containing from 0% to 35% inorganic halide in an alcohol wherein the concentration of alcohol is at least 40% by weight of the combined (a) and (b) solutions;
   (c) mixing and reacting the solutions of steps (a) and (b) at a temperature not in excess of 95° C. for a period of from about 1 to about 8 hours to form the polyvinylpyrrolidone-iodine complex simultaneously with an alcohol-water azeotrope;
   (d) removing the alcohol/water azeotrope while maintaining solids in the distilland below 40% by distillation and recycling distillate to step (b) and
   (e) drying the remaining product solution containing less than 40% solids from the distillation zone to provide a uniformly colored, particulate product of improved stability.

2. The process of claim 1 wherein the alcoholic solution is ethanol or a mixture of methanol and ethanol.

3. The process of claim 2 wherein the concentration of alcohol in the reaction solution of steps (a) and (b) is between about 50% and about 95%.

4. The process of claim 1 wherein the halogen of step (b) is iodine.

5. The process of claim 4 wherein the iodine contains up to 35% iodide as hydrogen iodide or an inorganic salt thereof.

6. The process of claim 1 wherein solids in the distilland are maintained between about 15% and about 30%.

7. The process of claim 6 wherein the distilland is spray dried at an air inlet temperature of from about 250° C. to about 400° C. under an air pressure of from about 4 Kg/cm² to about 7 Kg/cm².

* * * * *